United States Patent [19]

Farnham et al.

[11] Patent Number: 5,210,233

[45] Date of Patent: May 11, 1993

[54] CYCLIC PERFLUOROPOLYETHER

[75] Inventors: William B. Farnham, Hockessin; Ming-Hong Hung, Wilmington, both of Del.

[73] Assignee: E. I. Du Pont de Nemours and Company, Wilmington, Del.

[21] Appl. No.: 864,818

[22] Filed: Apr. 2, 1992

Related U.S. Application Data

[60] Division of Ser. No. 713,911, Jun. 12, 1991, Pat. No. 5,134,211, which is a continuation-in-part of Ser. No. 592,172, Oct. 9, 1990, Pat. No. 5,059,720, which is a division of Ser. No. 473,083, Jan. 31, 1990, Pat. No. 4,982,009.

[51] Int. Cl.$^5$ ............................................. C07D 323/00
[52] U.S. Cl. ...................................... 549/353; 549/352
[58] Field of Search ................................. 549/352, 353

[56] References Cited

U.S. PATENT DOCUMENTS 4,564,717  1/1986  Ohmori et al. ...................... 568/843

FOREIGN PATENT DOCUMENTS 199138    10/1986  European Pat. Off. .
63-002418  1/1988  Japan .

Primary Examiner—Nicky Chan
Attorney, Agent, or Firm—Barbara C. Siegell

[57] ABSTRACT

Novel hydroxy containing fluorovinyl ethers, polymers of hydroxy containing fluorovinyl ethers, novel cyclic ethers, copolymers of selected hydroxy containing fluorovinyl ethers, a process for reducing ester containing fluorovinyl compounds to the corresponding alcohol with borohydrides, and a process for polymerizing hydroxy containing fluorovinyl ethers are disclosed.

7 Claims, No Drawings

CYCLIC PERFLUOROPOLYETHER

This application is a divisional application of Ser. No. 713,911 (now U.S. Pat. No. 5,134,211), filed Jun. 12, 1991, which is a Continuation-In-Part of U.S. Ser. No. 592,172 (now U.S. Pat. No. 5,059,720), filed Oct. 9, 1990, which is a divisional application of Ser. No. 473,083 (now U.S. Pat. No. 4,982,009), filed on Jan. 31, 1990.

A process for reducing ester containing fluorovinyl compounds to the corresponding alcohol with alkali metal borohydrides, selected novel hydroxy containing fluorovinyl ethers, novel cyclic ethers, novel polymers of hydroxy containing fluorovinyl ethers, a process for making such polymers and novel copolymers of selected hydroxy containing fluorovinyl ethers are provided.

BACKGROUND OF THE INVENTION

Japanese Patent 88002418 reports the synthesis of 7,7-dihydro-7-hydroxy(perfluoro-3-oxahepten-1) by chlorinating the methyl ester of perfluoro(3-oxa-1-heptenoic acid), reduction of the chlorinated product with $NaBH_4$ to give the corresponding alcohol, and then reaction of the alcohol with zinc metal to regenerate the vinyl ether, which is the desired product. It is reported that this compound can be free radically copolymerized with at least one other fluorinated monomer, and optionally non-fluorinated monomers, to form useful polymers.

U.S. Pat. No. 4,564,717 reports the synthesis of compounds of the formula $CF_2=CF(CF_2)_m(CH_2)_nOH$ wherein m is an integer from 0 to 10 and n is an integer of 1 to 4. Among the methods of preparation described, is the reduction of the compound $CF_2X^1CFX^2CF_2COOR$ (sic) wherein R is alkyl and $X^1$ and $X^2$ are chlorine or bromine, by various reducing agents including alkali metal borohydrides. The olefin is then produced by dehalogenation of the alcohol with a metal such as zinc. In essence, in both this and the previous reference, the double bond has been "protected" by halogenating it (with chlorine or bromine) before the reduction step, and dehalogenating after the reduction step.

European Patent Application 135,917 discloses copolymers of vinylidene fluoride with a compound of the formula $CF_2=CF(CF_2)_m(CH_2)_nOH$ where m is 0 to 10 and n is 1–4, and optionally another fluorinated termonomer. Polymers of hydroxy containing fluorovinyl ethers are not mentioned.

European Patent Application 199,138 reports preparation and polymerization (with other fluorine containing olefins) of the compound $CF_2=CFO(CF_2CFYO)_n(CF_2CF_2CH_2O)_mCF_2CF_2CH_2X$, wherein X is hydrogen or halogen, Y is fluorine or $-CF_3$, m is an integer of 0 to 5 and n is 0, 1 or 2. No mention is made of a hydroxy group being present.

It is one object of the present invention to provide a simplified method for the production of hydroxy containing fluorovinyl compounds by the alkali metal borohydride reduction on the corresponding esters. It is an additional object to conduct the reduction process so protection of the double bond, as by halogenation, is unnecessary.

A further object of the invention is to homopolymerize hydroxy containing fluorovinyl ethers using anionic catalysts. It is an additional object to disclose polymers resulting from the polymerization of hydroxy containing fluorovinyl ethers.

Finally, it is also an objective of this invention to provide certain novel hydroxy containing fluorovinyl ethers and their copolymers with selected monomers.

These and other objects are achieved by the invention disclosed in the below specification and in the appended claims.

SUMMARY OF THE INVENTION

This invention concerns a process for the production of hydroxy containing fluorovinyl compounds, comprising, contacting in a solvent an alkali metal borohydride with a compound of the formula $CF_2=CFR^1CO_2R^2$ wherein $R^1$ is a covalent bond, a perfluoroalkylene group and $-OR^3$—wherein $R^3$ is a perfluoroalkylene group, and $R^2$ is hydrocarbyl or substituted hydrocarbyl. This invention further concerns hydroxy containing fluorovinyl ethers of the formula $CF_2=CF[OCF_2CF(CF_3)]_n(O)_p(CF_2)_mCH_2OH$ wherein p is 0 or 1, m is 0 to 10 and n is 1 to 20, provided that when m is 0, p is 0, and further provided that when m is greater than 0, p is 1. Also disclosed is a process for polymerizing hydroxy containing fluorovinyl ethers, comprising, contacting a selected catalyst with one or more hydroxy fluorovinyl ethers of the formula $CF_2=CFOR^4CF_2CH_2OH$, wherein $R^4$ is perfluoroalkylene. A polymer consisting essentially of the repeat formula $-[CF_2CFHOR^4CF_2CH_2O]-$, wherein $R^4$ is perfluoroalkylene. Also disclosed is a copolymer containing the hydroxy containing repeat unit

wherein p is 0 or 1, m is 0 to 10 and n is 1 to 20, provided that when m is 0, p is 0, and further provided that when m is greater than 0, p is 1, with other selected repeat units.

This invention also concerns cyclic ethers of the formula

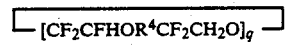

wherein $R^4$ is perfluoroalkylene and q is 2, 3 or 4.

DETAILS OF THE INVENTION

In accordance with the present invention, there is provided a process for the production of hydroxy containing fluorovinyl compounds, comprising, contacting in a solvent an alkali metal borohydride with a compound of the formula $CF_2=CFR^1CO_2R^2$ wherein $R^1$ is selected from a covalent bond, a perfluoroalkylene group and $-OR^3$—wherein $R^3$ is a perfluoroalkylene group, and $R^2$ is hydrocarbyl or substituted hydrocarbyl.

By "perfluoroalkylene group" herein is meant a bivalent saturated radical regarded as derived from a perfluorinated alkane by the removal of two fluorine atoms from different carbon atoms. The "perfluoroalkylene group" may also contain oxygen atoms between alkylene segments, to form one or more ether groups in each perfluoroalkylene group.

By "substituted hydrocarbyl" herein is meant any substituent in a hydrocarbyl group that will not interfere with the reduction reaction. However, even substituents that react with the alkali metal borohydrides may be present, provided enough borohydride is added to reduce the ester to the alcohol.

Preferred alkali metal borohydrides are lithium borohydride, sodium borohydride and potassium borohydride. The molar ratio of borohydride to ester is about 0.3 to about 1.2, preferably about 0.4 to about 0.8.

It is preferred that the solvent is an alcohol. Preferred alcohols are methanol and ethanol.

The process is carried out at about $-10°$ to about $+30°$ C., preferably about $0°$ to about $15°$ C. and most preferably about $5°$ to about $10°$ C. External cooling may be needed to maintain the correct temperature.

Any substantial amount of water should be excluded from the reaction, and it is convenient to carry out the reaction under an inert atmosphere such as nitrogen, in order to exclude moisture. Starting materials should be substantially dry. Agitation is preferred during the reaction, and it is preferred if the agitation is vigorous for efficient mixing.

Products may be isolated by standard techniques well known to those skilled in the art, such as distillation. Such techniques are illustrated in the Examples.

Typical procedures for preparing compounds of the formula $CF_2=CFR^1CO_2R^2$ are found U.S. Pat. No. 4,275,226; R. Sullivan in J. Org. Chem., vol. 34, pp. 1841-1844 (1969); U.S. Pat. No. 4,281,092; and U.S. Pat. No. 4,138,426.

In preferred embodiments $R^1$ is $—OR^3—$, wherein $R^3$ is $—(CF_2)_y—$, wherein y is 2 to 10; or $R^1$ is $—OR^3—$ wherein $R^3$ is $—[CF_2CF(CF_3)O]_x(CF_2)_z—$, wherein z is 1 to 10 and x is 1 to 20; or $R^1$ is perfluoroalkylene; or $R^1$ is a covalent bond. In an especially preferred embodiments $R^1$ is $—(CF_2)_q—$ wherein q is 1 to 10; or x is 1 and z is 2. In a preferred embodiment of the process $R^2$ is alkyl, and it is especially preferred if $R^2$ is alkyl in combination with any of the preferred embodiments of $R^1$. Unless otherwise noted, all numerical ranges that refer to chemical formulas herein, represent integers throughout those particular ranges, and not fractional values.

The hydroxy containing fluorovinyl compounds produced by the above process are useful as monomers in polymerization, and may be homo- or copolymerized (infra).

Also disclosed is a process for polymerizing hydroxy containing fluorovinyl ethers, comprising, contacting a base or another compound selected from the group consisting of bis(triphenylphosphoranylidene)-ammonium chloride, an alkali metal carbonate, $R^1_4NCl$, $(R^1_4N)_2CO_3$, $R^1_4NHCO_3$, and cesium fluoride, with one or more hydroxy fluorovinyl ethers of the formula $CF_2=CFOR^4CF_2CH_2OH$, wherein $R^4$ is perfluoroalkylene, and each $R^1$ is independently alkyl.

The polymers and cyclic ethers produced by this process are described below. By the word "polymerizing" in the paragraph immediately above is meant the production of linear polymeric or cyclic ethers. The formation of the cyclic ethers is favored by the use of solvents, and in particular, relatively dilute solutions during the polymerization. Linear polymer formation is favored by concentrated monomer solutions, and in particular, carrying out the process without solvent.

When a base is used, the polymerization process is preferably carried out in a solvent, preferably a polar but nonprotic solvent. Such solvents are well known to those skilled in the art, and include, but are not limited to N,N-dimethylformamide, dimethylsulfoxide, N,N-dimethylacetamide, tetrahydrofuran, the glymes, etc. N,N-dimethylformamide is preferred. Protic solvents, particularly those that contain a proton more acidic than the hydroxy group in the hydroxy containing fluorovinyl ethers should be avoided. The solvents, and indeed all starting materials should be substantially free of water.

The base used in the process should be one whose conjugate acid is less acidic than the hydroxy proton in the hydroxy containing fluorovinyl ether. The base should also be at least slightly soluble in the reaction medium, so that reaction may be affected. Such bases are well known to those skilled in the art, and include, but are not limited to alkali metal alkoxides, alkali metal hydrides, amines, etc. Alkali metal alkoxides and hydrides are preferred, and potassium t-butoxide is especially preferred. The molar ratio of hydroxy containing fluorovinyl ether to base is about 5 to about 200, preferably about 8 to about 50, most preferably about 10 to about 25.

When a base is used, the process is run at a temperature of about $-10°$ to about $+100°$ C., preferably about $0°$ to about $50°$ C., most preferably about $10°$ to about $30°$ C. Agitation is of the reaction mass preferred, preferred to mix separate phases.

It is believed that the base or "another compound" [bis(triphenylphosphoranylidene)ammonium chloride, an alkali metal carbonate, $R^1_4NCl$, $(R^1_4N)_2CO_3$, $R^1_4NHCO_3$, or cesium fluoride]act as catalysts for the polymerization process. In order to achieve maximum molecular weights of the polymer produced, and in particular to avoid significant production of cyclic dimer, trimer, etc., it is preferred if the catalyst is not a base.

Preferred other compounds are bis(triphenylphosphoranylidene)ammonium chloride, $R^1_4NCl$, wherein each $R^1$ is independently alkyl containing 1 to 6 carbon atoms, cesium fluoride, cesium carbonate and potassium carbonate. When other compounds are used as catalysts, and to obtain high molecular weight polymer, it is preferred if the process is run with little or no solvent (neat). Also in order to obtain high molecular weight, it is preferred if the monomer is highly purified. This purification can usually be accomplished by distillation. (For example, the monomer EVEOH [perfluoro(9,9-dihydro-9-hydroxy-3,6-dioxa-5-methylnon-1-ene)]may be distilled through a spinning band column, boiling point about 78° C. at 27 mm pressure. For best results the middle fractions should be used.)

When "another compound", as defined on page 7, lines 14–17, above, is used as the catalyst, the preferred temperature is about 80° C. to about 150° C., more preferably about 100° C. to about 120° C. Since the polymerization is exothermic, care should be taken to provide adequate cooling, especially when the polymerization is run neat.

When TM another compound TM is used as the catalyst it is preferred if the catalyst is about 0.1 to about 10 percent by weight, more preferably about 0.2 to about 4 percent by weight of the hydroxy fluorovinyl ether present.

The product polymers may be isolated by techniques well known to those skilled in the art, such as evaporation of solvent. Such techniques are illustrated in the Examples.

In preferred hydroxy containing fluorovinyl ethers used in the process $R^4$ is $—(CF_2)_s—$, wherein s is 1 to 10;

or $R^4$ is $—[CF_2CF(CF_3)O]_t(CF_2)_u—$, wherein u is 1 to 10 and t is 1 to 20. In an especially preferred embodiment t is 1 and u is 1, or s is 2.

This invention also concerns a cyclic ether of the formula

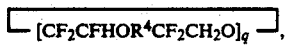

wherein $R^4$ is perfluoroalkylene and q is 2, 3 or 4. In preferred cyclic ethers, n is 2. In other preferred cyclic ethers $R^4$ is $—(CF_2)_s—$, wherein s is 1 to 10, and it is especially preferred if s is 2. In another preferred cyclic ether, $R^4$ is $—[CF_2CF(CF_3)O]_t(CF_2)_u—$, wherein u is 1 to 10 and t is 1 to 20, and it is especially preferred if t is 1 and u is 1. The cyclic ethers are made by the process described immediately above. The cyclic ethers are useful as lubricants. They may also be fluorinated to form perfluorinated cyclic ethers which are useful as lubricants and heat transfer fluids (as described in copending commonly assigned application Ser. No. 07/713,926, filed of even date with this application). The cyclic ethers of this invention are therefore useful as intermediates for the production of such perfluorinated cyclic ethers.

A polymer consisting essentially of the repeat formula $—[CF_2CFHOR^4CF_2CH_2O]—$, wherein $R^4$ is perfluoroalkylene.

In preferred polymers $R^4$ is $—(CF_2)_s—$, wherein s is 1 to 10; or $R^4$ is $—[CF_2CF(CF_3)O]_t(CF_2)_u—$, wherein u is 1 to 10 and t is 1 to 20. In an especially preferred embodiment t is 1 and u is 1, or s is 2.

These polymers are useful as lubricants, lubricant precursors, macromonomers and coatings. These polymers are made by the process described immediately above.

A copolymer comprising the hydroxy containing repeat unit

wherein p is 0 or 1, m is 0 to 10 and n is 1 to 20, provided that when m is 0, p is 0, and further provided that when m is greater than 0, p is 1, and one or more other repeat units.

Such a repeat unit, which has a hydroxy contained within it, is useful as a reactive site along the polymer chain to accomplish processes such as crosslinking, or may change the surface characteristics of a polymer while leaving the bulk properties relatively unchanged. Thus in many cases the above repeat unit will be present in the polymer in only relatively small amounts, about 0.001 to about 30 mole percent, preferably about 0.05 to about 15 mole percent.

It is especially useful in crosslinking relatively unreactive polymers, such as fluoropolymers. Thus it can be incorporated into polymers containing repeat units derived from monomers selected from the group consisting of tetrafluoroethylene; hexafluoropropylene and vinylidene fluoride; hexafluoropropylene, vinylidene fluoride and tetrafluoroethylene; ethylene and vinylidene fluoride; perfluoro(methyl vinyl ether) and tetrafluoroethylene; perfluoro(methyl vinyl ether) and hexafluoropropylene; chlorotrifluoroethylene; ethylene and chlorotrifluoroethylene; vinylidene fluoride; tetrafluoroethylene and propylene; tetrafluoroethylene and ethylene; tetrafluoroethylene and hexafluoropropylene; perfluoro-2,2-dimethyl-1,3-dioxole; perfluoro-2,2-dimethyl-1,3-dioxole and tetrafluoro-ethylene; vinyl fluoride; tetrafluoroethylene and perfluoro[2-(fluorosulfonylethoxy)propyl vinyl ether]; and vinyl acetate and tetrafluoroethylene. In the immediately above listing of monomers, each of the monomer(s) between the semicolons represents a specific copolymer of the hydroxy containing fluorovinyl ether with that particular monomer or combination of monomers. By "incorporated into polymers" in the sentence above is meant that when the above polymers (and others not specifically mentioned) are formed by free radical polymerization, the appropriate amount of hydroxy containing fluorovinyl ether monomer is added to the polymerization reaction to be copolymerized with the other monomer(s). It will be noted that the polymers above contain fluoromonomers. The term fluoromonomers means a monomer containing a vinyl group to which at least 1 fluorine atom is directly bound (i.e. has one or more vinylic fluorine atoms). Copolymers of the hydroxy containing fluorovinyl ethers with fluoromonomers, and optionally other monomers, are preferred. Also preferred are copolymers with vinyl esters, and especially preferred is vinyl acetate. Such polymers are useful for example, as molding resins (when plastic) and elastomers (where the "base" polymer is an elastomer).

These copolymers can be made by methods well known to those skilled in the art. Further illustrations of typical polymerizations processes are given in the Examples.

In the following Examples, the following abbreviations and terms are used:
Bu —n-butyl
t-BuOK —potassium t-butoxide
dispersion factor —weight average molecular weight/number average molecular weight
DMF —N,N-dimethylformamide
DP —degree of polymerization (equal to Mn divided by the monomer molecular weight)
DSC —differential scanning calorimetry
EtOH —ethanol
EVE —methyl perfluoro (4,7-dioxa-5-trifluoromethylhept -8-enocite)
EVE alcohol —perfluoro (9,9-dihydro-9; -hydroxy-3,6-dioxa-5-trifluoromethylnon -1-ene)
EVEOH —perfluoro(9,9-dihydro-9-hydroxy-3,6-dioxa-5-trifluoromethylnon -1-ene
F-113 —1,1,2-trichloro-1,2,2-trifluoroethane
GC —gas chromatography
GPC —gel permeation chromatorgraphy
Me —methyl
Mn —number average molecular weight
MS —mass spectrum
$M_w$—weight average molecular weight
PDD —perfluoro(2,2-dimethyl-1,3-dioxole) (Can be made by methods described in U.S. Pat. Nos. 3,865,845, 3,978,030 and 4,393,227)
PMMA —poly(methyl methacrylate)
PPN —bis(triphenylphosphoranylidene)ammonium, $[(C_6H_5)_3P—N=P(C_6H_5)_3]^+$
TFE —tetrafluoroethylene
Tg —glass transition temperature
Tm —melting temperature
VAc —vinyl acetate

EXAMPLE 1

Preparation of
9,9-Dihydro-9-hydroxy-perfluoro-(3,6-dioxa-5-methyl-1-nonene)($CF_2$=CFO—$CF_2$CF($CF_3$)O—$CF_2CF_2$—$CH_2$OH):

To a dry flask was charged EVE (211 g, 0.50 mole) in absolute ethanol (300 ml) with a magnetic stirring bar. Sodium borohydride (11.34 g, 0.30 mole) was added slowly from a solid addition funnel. The reaction was somewhat exothermic and the reaction pot was kept at $\leq 10°$ C. by external cooling. After the addition of sodium borohydride was completed, the reaction mixture was stirred for 1 hr at room temperature. The pot mixture was then dumped into an ice water (600 ml)/6N HCl (600 ml) mixture. The bottom product layer was separated, washed with water and distilled to give the desired product as a clear, colorless liquid. Bp. 68° C/25 mmHg. Yield: 168.7 g (85.6 %). H-1 NMR($CDCl_3$): 4.00 (dt, J =1.0 Hz, 13.5 Hz, 2H), 2.12 (s, br, 1H ); F-19 NMR ($CDCl_3$, F-11 internal standard): $-80.4$ (s, br, 3F), $-84.2$ (s, br, 2F), $-85.3$ (m, br, 2F), $-126.6$ (t, J =14 Hz, 2F), $-145.7$ (t, J =21.8 Hz, 1F), $-113.4$, $-113.7$, $-113.8$, $-114.2$ (4s, 1F), $-121.6$, $-112.1$, $-122.2$, $-122.7$ (4t, J =5.2 Hz, 1F), $-135.3$, $-135.6$, $-135.9$, $-136.2$ (4t, J =5.8 Hz, 1F).

EXAMPLE 2

Preparation of
9,9-Dihydro-9-hydroxyperfluoro-(3,6-dioxa-5-methyl-1-nonene)

EVE (21.1 g, 0.05 mole) was dissolved in absolute ethanol (15 ml) at 0° C. In a separate flask was charged sodium borohydride (1.15 g, 0.03 mole) in absolute ethanol (20 ml) at 0° C. The $NaBH_4$/EtOH solution was added slowly into EVE/EtOH solution while the pot temperature was kept between 0° to 5° C. After addition, the reaction mixture was stirred for 15 min at room temperature. The product was worked up as described in Example 1 and distilled to give the clear, colorless product 11.7 g (59.4% yield) as a liquid. Bp. 70° C./25 mmHg.

EXAMPLE 3

Preparation of
7,7-Dihydro-7-Hydroxyperfluoro(3-Oxa-1-Heptene)($CF_2$=CFO—$CF_2CF_2CF_2$—$CH_2$OH)

To a dry flask was charged methyl perfluoro (5-oxa-6-heptenoate) (61.2 g, 0.2 mole) in absolute ethanol (120 ml). Sodium borohydride (4.54 g, 0.12 mole) was added slowly into the reaction solution via a solid additional funnel while the temperature was kept at about 10° C. The mixture was allowed to stir at room temperature for 1 hr after the addition of $NaBH_4$ was completed. The mixture was then dumped into ice water/6NHCl (1:1 v/v, 500 ml) and worked up. The product was isolated by final distillation. 47.6 g (85.6% yield) of the desired product was obtained as a clear, colorless liquid. Bp. 54°-55° C./30 mmHg. H-1 NMR ($CDCl_3$): 4.10 (t, J =14.5 Hz, 2H); 2.65 (s, br, 1H); F-19 NMR (188.24 MHz, $CDCl_3$): $-85.7$(m, 2F), $-123.4$ (m, 2F), $-127.6$ (s, br, 2F), $-113.7$, $-114.1$, $-114.2$, $-114.5$ (4m, 1F), $-121.8$, $-122.3$, $-122.4$, $-122.9$ (4t, J =5.6 Hz, 1F), $-134.9$, $-135.2$, $-135.5$, $-135.8$ (4t, J =5.6 Hz, 1F).

EXAMPLE 4

Homopolymerization of $CF_2$=CFO—$CF_2$CF($CF_3$)O-$CF_2CF_2$—$CH_2$OH:

Potassium t-butoxide (0.112 g, 0.001 mole) was dissolved in N,N-dimethyl formamide(DMF) (10 ml) and was cooled to 0° C. The title vinyl ether alcohol (7.88 g, 0.02 mole) in DMF (4 ml) was added slowly into the above solution via syringe. The reaction was maintained between at 10° to 25° C. via external cooling. After the addition was finished, the mixture was stirred for 2 hrs at about 10° C., then warmed up gradually to room temperature and was continued at ambient temperature for 6 hrs. The product mixture was dumped into ice water and was extracted with ether. The ether layer was separated, washed thoroughly with water and dried over magnesium sulfate. Ether solvent was removed in vacuo and the product polymer was further dried under high vacuum. 4.24 g (53.8 % yield) of polymeric viscous oil was obtained. The weight average molecular weight was determined to be 4,100 with dispersion factor 1.51 by GPC with PMMA as the reference standard. The structure of the product was supported by its H-1 and F-19 NMR spectroscopic data.

EXAMPLE 5

Homopolymerization of
$CF_2$=CFO—$CF_2$CF($CF_3$)O-$CF_2CF_2$—$CH_2$OH

The title vinyl ether alcohol (7.88 g, 0.02 mole) was polymerized with potassium t-butoxide (0.112 g, 0.001 mole) in DMF as described in Example 4. After warmed to room temperature, the reaction mixture was stirred at ambient temperature for 48 hrs instead of 6 hrs. After working up, the polymeric oil was determined to have weight average molecular weight 5,920 with a dispersion factor 1.74 by GPC with PMMA as reference standard.

EXAMPLE 6

Homopolymerization of
$CF_2$=CFO—$CF_2CF_2CF_2$—$CH_2$OH

Potassium t-butoxide (0.112 g, 0.001 mole) was dissolved in DMF (10 ml) at 10° C. The alcohol substrate (5.56 g, 0.02 mole) in DMF (4 ml) was added slowly into the t-BuOK/DMF solution slowly via syringe. After stirring for 2 hrs at 10° C., the reaction mixture was warmed slowly to room temperature. Some exotherm was observed when temperature reached 25° C. The reaction mixture was cooled and kept stirring for 6 hrs at room temperature. The product was then dumped into ice water and was worked up as previously described. 4.13 g (74.3 % yield) of pale-yellow viscous polymeric oil was obtained. The weight average molecular weight of this polymer was determined to be 4,970 with dispersion factor 2.00 by GPC by the use of PMMA as the reference standard.

EXAMPLE 7

Free Radical Copolymerization of EVE Alochol with TFE

In a shaker tube was charged EVE Alcohol (10 g, 0.0254 mole), 1,1,2-trichloro-1,2,2-trifluoroethane (F-113) (60 g, 0.32 mole) and 4,4'-bis(t-butylcyclo-hexyl)-peroxy dicarbonate (0.05 g). The tube was sealed, cool-evacuated and tetrafluoroethylene (10 g, 0.1 mole) was then charged. The tube was sealed again and was heated at 50° C., 60° C. and 70° C. for 2 hrs respectively with shaking. The solvent was removed from the unloaded polymer solution and the polymer was finally dried in a vacuum oven (ca. 150 mmHg) at 120° C. for 24 hrs. White polymer, 9.0 g, was obtained. The polymer has a Tm at 240° C. as measured by DSC. The composition of this polymer was determined to be TFE/EVE alcohol =87/13 (mole %) by F-19 high temperature NMR spectroscopy.

EXAMPLE 8

Free Radical Copolymerization of EVE Alcohol with TFE

In the shaker tube was charged EVE alcohol (10 g, 0.0254 mole), F-113 solvent (20 g, 0.107 mole) and 4,4'-bis(t-butylcyclohexyl)peroxy dicarbonate (0.03 g tube was sealed and cool-evacuated and tetrafluoro-ethylene was charged in. The tube was heated to 45° C. and the pressure of tetrafluoroethylene maintained at 60 psi. The tube was shaken for 6 hrs and was worked up as in Example 7. 3.3 g of the white polymer was obtained. This polymer has shown a Tg at 164° C. as determined by DSC, and have a composition of TFE/EVE alcohol =74/26 (mole %) as determined by F-19 high temperature NMR spectroscopy.

EXAMPLE 9

Free Radical Copolymerization of EVE Alcohol and TFE

This polymerization was carried out with EVE alcohol monomer (4 g, 0.0102 mole), F-113 (72 g, 0.417mole ), 4,4'-bis(t-butylcyclohexyl)peroxy dicarbonate (0.05 g) and tetrafluoroethylene (20 g, 0.2 mole) in a shaker tube at 50° C., 2 hrs; 60° C., 2 hrs and 70° C., 2 hrs. 17.3 g of white polymer was obtained. The polymer has a Tm at 318.3° C. as shown by DSC and has a composition of EVE alcohol 98.5-99.0/1.5-1.0 (mole %) as determined by F-19 NMR.

EXAMPLE 10

Free Radical Copolymerization of EVE Alcohol and PDD

This polymerization was carried out with EVE alcohol (5 g, 0.0127 mole) and PDD (30 g, 0.123 mole) in F-113 (100 g, 0.533 mole) with 4,4'-bis(t-butylcyclohexyl)peroxy dicarbonate (0.06 g) initiator under the same temperature as described in Example 9. White polymer 6.3 g was obtained after workup. This polymer has a Tg at 210° C. The composition of this polymer was determined to be PDD/EVE alcohol =96.5/3.5, (mole %) by F-19 NMR.

EXAMPLE 11

Free Radical Copolymerization of EVE Alcohol, TFE and VAc

In the shaker tube was charged EVE alcohol (10 g, 0.0254 mole), VAc (40 g, 0.465 mole), F-113 (120 g, 0.64 mole) and 4,4'-bis(t-butylcyclohexyl)peroxy dicarbonate (0.1 g). The tube was sealed and tetrafluoroethylene (4 g, 0.04 mole) was added after the tube was cooled and evacuated. The tube was resealed and was heated at 60° C. for 6 hrs. The resulting polymer solution was dissolved in acetone and precipitated with ice water. The polymer was collected by filtration and washed with water and was dried under nitrogen purge at ambient temperature. White solid polymer 48.7 g was obtained. The polymer has a Tg at 40.6° C. by DSC and the polymer has a composition of VAc/TFE/EVE alcohol =62.8/27.6/9.6 (mole %) as calculated from its H-1 & F-19 NMR spectroscopic data. The structure of the polymer was also supported by its IR spectrum.

EXAMPLE 12

Free Radical Copolymerization of EVE Alcohol, TFE and PDD

This experiment was carried out with EVE alcohol (2 g, 0.0051 mole), PDD (51 g, 0.209 mole) and tetrafluoroethylene (1 g, 0.01 mole) in F-113 (165 g, 0.88 mole) by the use of 4,4'-bis(t-butylcyclo-hexyl)peroxy dicarbonate initiator (0.2 g) in a shaker tube at 50° C., 60° C. and 70° C. for 2 hrs respectively. 44.9 g of white polymer was obtained after working up. This polymer has shown a Tg at 224.3° C. by DSC.

EXAMPLE 13

EVEOH Cyclic Dimer

A mixture of tetraglyme (5 mL) and oil-free potassium hydride (5 mg) was treated dropwise with EVEOH (1.0 g, 2.5 mmol). GC analysis (25 m methyl silicone gum capillary column, 60°-250° C. at 20 deg/min) after 4 h showed no starting material and several components with ca. 10 min retention time. The reaction mixture was treated with water, extracted with F-113, and the extract was washed several times with water, dried, and evaporated to give 1.0 g of colorless oil. Kugelrohr distillation (0.2 mm, to 100 deg) gave ca. 100 mg of oil. $^{19}F$ NMR (acetone-$d_6$): −79.5 (m, $CF_3$), −82.2 to −85.0 and −85.3 to −87.0 (overlapping AB patterns, $OCF_2$), −89.4 to −92.5 (m, upfield portion of overlapping AB patterns), −122.8 to −123.8 (m, $CF_2CH_2$), −143.0 to −143.8 and −144.6 to −146.4 (m, CFH and CF($CF_3$)). GC/MS showed for the cyclic dimer a parent ion with m/z=787.974152 (calcd for $C_{16}H_6F_{26}O_6$=787.974922: for the cyclic trimer a parent ion with m/z=1181.952957 (calcd for $C_{24}H_9F_{39}O_9$=1181.962383); for the cyclic tetramer a parent ion with nominal m/z=1579.

The reaction described above was repeated using glyme (5 mL) as solvent. After 18 h, work-up (dilution with ether, addition of water) and Kugelrohr distillation (0.1 mm) gave 0.58 g, bp 80–92, and 0.13 g, bp 140–155.

A larger scale reaction using 6.0 g EVEOH, 30 mg KH, and 35 mL glyme provided 2.56 g of cyclic dimers.

EXAMPLE 14

Polymerization of EVEOH with $Cs_2CO_3$ $Cs_2CO_3$ (10 mg) and EVEOH (1.0 g) were placed in a vial, sealed, and heated in an oil bath maintained at 120° C. Within 1 hr, the mixture had thickened considerably. The reaction mixture was maintained at 120° C. for 88 hr. $^1H$ NMR (THF-$d_8$): 6.65 (d, J=52 Hz, CHF), 4.58 (t, J=13Hz, internal $CF_2CH_2O$), 3.90 (triplet J=ca 13Hz, CHF), 4.58 (t, J=13Hz, internal $CF_2CH_2O$), 3.90 (triplet J=ca 13Hz, terminal $CH_2O$); integrated area of internal $CH_2O$ to terminal $CH_2O$ groups was ca. 55/1. Size exclusion analysis showed the major peak (90%) with Mn=27,200 and Mw=57,900 using polystyrene standards. $^{19}F$ NMR featured internal $CF_2CH_2O$(−123.6) and terminal $CF_2CH_2O$ groups (−125.6) in relative areas of 126/1. No signals for residual trifluorovinyl groups were observed. NMR and size exclusion analyses were in reasonably good agreement and were consistent with the desired linear condensation polymer $(CF_2CHFOCF_2CF(CF_3)OCF_2CF_2CH_2O)_n$. TGA of a similarly prepared sample showed onset of thermal decomposition at ca. 300° C. (air) and 400° C. (N2). DSC exhibited Tg at −60° C.

EXAMPLE 15

Polymerization of EVEOH with Me$_4$NCl

Me$_4$NCl (2 mg) and EVEOH (1.0 g) were placed in a vial, sealed, and heated in an oil bath at 107° C. for 65 hr. $^1$H NMR analysis of the colorless, viscous grease showed the ratio of signals at 4.6 ppm and 3.90 ppm as ca. 60/1. The small amount of cyclic dimer formed (GC analysis) was removed by kugelrohr distillation (up to 110° C./0.05 mm). 19F NMR featured the internal/terminal $CF_2CH_2O$ group ratio as ca. 83/1. Size exclusion analysis showed the major peak with Mn=26,700 and Mw=52,800, consistent with EVEOH condensation polymer, of the formula shown in Example 14.

EXAMPLE 16

Polymerization of EVEOH with PPNCl

PPNCl (5 mg) and EVEOH (1.0 g) were placed in a vial, sealed and heated at 120° C. for 18 h r. $^1$H NMR analysis featured the ratio of 4.60/3.90 signals as ca. 59/1 (assignments discussed in Example 14). $^{19}$F NMR featured ratio of −123.7/−125.6 signals as ca. 75/1 Size exclusion analysis featured the major component with Mn=20,200, Mw=37,800, consistent with the EVEOH condensation polymer.

EXAMPLE 17

Polymerization of EVEOH with Potassium Carbonate

K$_2$CO$_3$ (30 mg) and EVEOH (1.0 g) were placed in a vial, sealed and heated at 50° C. for 0.5 hr and then at 100° C. for 18 hr. $^{19}$F NMR showed the signals described in Example 14 with additional signals at −121.6, −136.0, −137.4, −143.5 and −147.0. Size exclusion analysis had Mw=8570, Mn=6120.

EXAMPLE 18

Polymerization of EVEOH with Tetrabutylammonium Bicarbonate

Tetrabutylammonium bicarbonate was prepared as described below: A solution of tetrabutylammonium chloride (3.0 g, 11.5 mmol) in methanol (25 mL) was treated with potassium carbonate (0.78 g, 5.7 mmol) and stirred for 18 hr. The mixture was filtered and stripped. Under dry nitrogen, the residue was taken up in CH$_3$CN, filtered, and partially evaporated. Ether was added, and the resulting solid was separated, triturated with ether, and filtered to give an off-white solid, mp 90–115 deg. IR (nujol mull) featured a significant band at 1673 cm$^{-1}$. (Lit reference = Inorg. Chem., Vol. 28, p. 1231 (1989) for IR comparison.)

A mixture of EVEOH (1.0 g) and tetrabutylammonium bicarbonate (10 mg) was prepared in a vial, sealed and heated to 80° C. for 15 min and then 120° C. for 18 hr. $^1$H NMR analysis showed the ratio of in-chain CH$_2$O/terminal CH$_2$OH groups to be ca. 50/1. $^{19}$F NMR was likewise in accord with the EVEOH condensation polymer. Size exclusion analysis showed Mw=34, 500; Mn=17, 200.

EXAMPLE 19

Polymerization of EVEOH with Bu$_4$NCl

EVEOH (1.0 g) and tetrabutylammonium chloride (2 mg) were placed in a vial, sealed and heated to 107° C. for 65 hr. $^1$H NMR analysis showed the ratio of in-chain CH$_2$O/terminal CH$_2$OH groups to be ca. 60/1. Size exclusion analysis showed Mw=46,700; Mn=24,000. Tg=ca. −60° C.

EXAMPLE 20

Polymerization of EVEOH with (PPN)$_2$CO$_3$

PPN carbonate was prepared as follows: Silver carbonate (1.38 g) was added to a solution of PPN chloride (5.74 g) in dry acetonitrile (40 mL) and the resulting mixture was stirred vigorously for 2 hr, filtered and evaporated to give 3.18 g of light tan solid. The product was triturated with THF and filtered to give 2.3 g of off-white solid. IR (KBr) showed a band at 1640 cm$^{-1}$.

EVEOH (1.0 g) and PPN carbonate (2 mg) were mixed in a vial and heated at 50° C. (20 min), 80° C. (30 min), and 120° C. for 16 hr. NMR spectra were in accord with EVEOH homopolymer, and indicated DP ca. 100–120. Size exclusion analysis showed Mw=52,100, Mh=22,900.

EXAMPLE 21

Polymerization of EVEOH with Cesium Fluoride

EVEOH (1.0 g) and cesium fluoride (4 mg) were mixed in a vial, sealed, and heated for 18 hr. $^{19}$F NMR showed the ratio of internal CF$_2$CH$_2$/terminal CF$_2$CH$_2$OH groups to be ca. 57/1. Size exclusion analysis showed Mw=31,100; Mn=16,700.

EXAMPLE 22

Polymerization Using Purified EVEOH

A sample of EVEOH (7.85 g, 19.9 mmol) was treated in small portions with bromine (3.2 g, 20 mmol), controlling the temperature at 15–22 deg. When the reaction was judged to be complete by GC analysis, excess bromine was removed under a stream of nitrogen and the product was isolated by kugelrohr distillation, 50° C./0.2 mm, providing 8.70 g. $^{19}$F NMR (THF-d$_8$): −164.13 (m, 2F, CF$_2$Br), −72.2 (apparent doublet of quartets, J=24, J=9 Hz) and −72.55 (apparent doublet of quartets J=23, 9 Hz, 1F, CFBr for two diastereomers), −80.5 to −86.2 (group of overlapping AB patterns, 4F, OCF$_2$), −79.4 (apparent quartet, J=9, 3F), −125.38 (t, J=14.8 Hz, 2F), −145.4 (m, 1F, tertiary CF), consistent with the desired dibromo alcohol.

A slurry of activated zinc dust (2.72 g, 41.6 mmol) and DMF (15 mL) was treated in portions with dibromoethane (1.05 g, 5.6 mmol) and stirred for 0.5 hr at ambient temperature. DibromoEVEOH (distilled, 10.0 g, 18 mmol) was added and the mixture was stirred for 1.25 hr, filtered, and the filtrate was added to water. The lower layer was separated, washed with water, and dried (MgSO$_4$). Traces of remaining water were removed by contact with activated sieves, and the product was kugelrohr distilled. NMR analysis did not detect contamination by other fluorinated alcohols.

A sample of the above EVEOH (1.0 g) and Cs$_2$CO$_3$ (4 mg) were mixed and processed as described in Example 14 (100° C./1 hr, 120° C./15 hr). Endgroup analysis by NMR suggested a value of DP above 200. Size exclusion analysis showed slightly higher values of Mw (65,500) and Mn (28,500) than were determined for other examples.

Although preferred embodiments of the invention have been described hereinabove, it is to be understood that there is no attempt to limit the invention to the precise constructions herein disclosed, and it is to be further understood that the right is reserved to all changes coming within the scope of the invention as defined by the appended claims.

What is claimed is:

1. A cyclic ether of the formula

$$\underset{\phantom{X}}{\overline{\phantom{XXXXXXXXXXXXXXXXXXX}}}[CF_2CFHOR^4CF_2CH_2O]_q\underset{\phantom{X}}{\overline{\phantom{X}}},$$

wherein $R^4$ is perfluoroalkylene or perfluoroalkylene containing one or more ether oxygen atoms, and q is 2, 3, or 4.

2. A cyclic ether as recited in claim 1 wherein said q is 2.

3. A cyclic ether as recited in claim 1 wherein said $R^4$ is $-(CF_2)_s-$, wherein s is 1 to 10.

4. A cyclic ether as recited in claim 3 wherein said s is 2.

5. A cyclic ether as recited in claim 1 wherein said $R^4$ is $-[CF_2CF(CF_3)O]_t(CF_2)_u-$, wherein u is 1 to 10 and t is 1 to 20.

6. A cyclic ether as recited in claim 5 wherein said t is 1, and said u is 1.

7. A cyclic ether as recited in claim 6 wherein said q is 2.

* * * * *